United States Patent
Pathak et al.

(10) Patent No.: US 12,357,245 B2
(45) Date of Patent: Jul. 15, 2025

(54) AUTOMATED PROCESS FOR CONTROLLING IN VIVO EXAMINATION OF THE CERVIX AND COLLECTING IMAGE DATA RELATED THERETO

(71) Applicant: NSV, Inc., Allentown, PA (US)

(72) Inventors: Soham Pathak, Allentown, PA (US); Ankita Shastri, Bothell, WA (US); Neha Kumar, Macungie, PA (US); Jeremy Lim, Emmaus, PA (US)

(73) Assignee: NSV, INC., Allentown, PA (US)

( * ) Notice: Subject to any disclaimer, the term of this patent is extended or adjusted under 35 U.S.C. 154(b) by 636 days.

(21) Appl. No.: 17/765,290

(22) PCT Filed: Sep. 30, 2020

(86) PCT No.: PCT/US2020/053368
§ 371 (c)(1),
(2) Date: Mar. 30, 2022

(87) PCT Pub. No.: WO2021/067334
PCT Pub. Date: Apr. 8, 2021

(65) Prior Publication Data
US 2022/0338714 A1    Oct. 27, 2022

Related U.S. Application Data

(60) Provisional application No. 62/909,878, filed on Oct. 3, 2019.

(51) Int. Cl.
*A61B 1/00* (2006.01)
*A61B 1/045* (2006.01)
(Continued)

(52) U.S. Cl.
CPC .......... *A61B 5/7435* (2013.01); *A61B 1/0004* (2022.02); *A61B 1/303* (2013.01); *G16H 30/40* (2018.01)

(58) Field of Classification Search
CPC ..... A61B 5/7435; A61B 1/0004; A61B 1/303; A61B 1/045; G16H 30/40; G16H 20/40
See application file for complete search history.

(56) References Cited

U.S. PATENT DOCUMENTS 5,895,358 A * 4/1999 Becker ................ G01S 7/52071
600/456
6,004,276 A * 12/1999 Wright .................. G16H 15/00
128/923

(Continued)

FOREIGN PATENT DOCUMENTS

WO  WO 2015173676    11/2015
WO  WO 2016207906    12/2016

(Continued)

*Primary Examiner* — Alexei Bykhovski
(74) *Attorney, Agent, or Firm* — Millen, White, Zelano & Branigan P.C.; William F. Nixon

(57) ABSTRACT

A colposcopy instrument (which includes a display screen) is controlled by a specific set of steps defined in software to follow a defined protocol for performing a colposcopy examination. The software is utilized to also control the features of an included camera so that consistent digital images are recorded. The integrated software prompts the medical personnel performing the colposcopy procedure to capture relevant images in an automated sequence that includes, for example, capturing a sequence of images after the application of the acetic acid to the cervix. The displayed user interface guides the individual performing the exam through a series of easy-to-understand screen prompts to capture specific, critical images during the exam. The process, once begun, is automated and does not require the individual performing the exam to make any decisions about whether or not to record a certain image.

20 Claims, 18 Drawing Sheets

(51) Int. Cl.
*A61B 1/303* (2006.01)
*A61B 5/00* (2006.01)
*G16H 30/40* (2018.01)

(56) References Cited

U.S. PATENT DOCUMENTS

| | | | | |
|---|---|---|---|---|
| 6,101,408 | A * | 8/2000 | Craine | A61B 5/0086 |
| | | | | 382/128 |
| 6,277,067 | B1 | 8/2001 | Blair | |
| 7,620,893 | B2 | 11/2009 | Forstmann et al. | |
| 8,487,987 | B2 | 7/2013 | Schute et al. | |
| 10,045,731 | B2 | 8/2018 | Prasad et al. | |
| 2004/0010515 | A1* | 1/2004 | Sawafta | G16H 50/70 |
| 2009/0034824 | A1* | 2/2009 | Li | G06T 7/0012 |
| | | | | 382/133 |
| 2009/0076368 | A1* | 3/2009 | Balas | A61B 1/00149 |
| | | | | 600/407 |
| 2013/0002903 | A1* | 1/2013 | Manico | H04N 23/66 |
| | | | | 348/222.1 |
| 2013/0006095 | A1 | 1/2013 | Jenkins et al. | |
| 2014/0372955 | A1* | 12/2014 | Berry | A61B 5/4824 |
| | | | | 715/835 |
| 2015/0073213 | A1* | 3/2015 | Khait | A61B 1/00036 |
| | | | | 600/109 |
| 2016/0058362 | A1* | 3/2016 | Wang | A61B 5/743 |
| | | | | 600/476 |
| 2016/0100909 | A1* | 4/2016 | Wollowick | A61B 6/505 |
| | | | | 600/424 |
| 2018/0325598 | A1* | 11/2018 | Strongosky | A61B 34/10 |

FOREIGN PATENT DOCUMENTS

| | | |
|---|---|---|
| WO | WO 2019030749 | 2/2019 |
| WO | WO 2019070998 | 4/2019 |
| WO | WO 2019145951 | 8/2019 |

* cited by examiner

AUTOMATED PROCESS FOR CONTROLLING IN VIVO EXAMINATION OF THE CERVIX AND COLLECTING IMAGE DATA RELATED THERETO

CROSS-REFERENCE TO RELATED APPLICATIONS

This application claims the benefit of U.S. Provisional Application No. 62/909,878, filed Oct. 3, 2019 and herein incorporated by reference.

TECHNICAL FIELD

The present invention relates to in vivo examination of the cervix as performed during a precancer screening/colposcopy procedure and, more particularly, to the utilization of a software-controlled tool to assist the individual performing the procedure to follow a preferred set of process steps.

BACKGROUND OF THE INVENTION

Abnormal growth of potential precancerous cells in the cervix exhibit certain morphologic features that can be identified during a colposcopic exam, which is a procedure to examine an illuminated, magnified view of the cervix (as well as the vagina and vulva). Acetic acid (and, perhaps, iodine) solutions may be applied to the surface of the cervix to improve visualization of specific abnormal growths.

Virtually all cervical precancer lesions become a transient and opaque white color with the application of 3-5% acetic acid. The whitening process (also referred to as "acetowhitening") occurs over time and is visible to the naked eye (or with the assistance of a low-level magnification). Thus, the individual performing the colposcopy is able to subjectively discriminate between abnormal and normal tissue.

Due to this subjective nature of a colposcopic examination, however, the accuracy of colposcopy has been found to be highly dependent upon the medical personnel's experience and expertise. Additionally, the specific process steps used during a colposcopy are not well-controlled and as a result it may be difficult to reproduce the same result for a given patient. Most conventional colposcopes do not provide quantitative diagnostic information, but rely instead on the experience and visual acuity of the examiner, potentially leading to high levels of variability (subjectivity) and error in diagnosis.

This problem is only exacerbated when the examination takes place in a part of the world that has little medical training, and may not have anyone other than a technician available to perform the procedure.

SUMMARY OF THE INVENTION

The present invention addresses the concerns regarding variabilities present in colposcopy, in the form of a software-controlled tool to assist the individual performing the procedure to follow a preferred set of process steps.

As mentioned above, the lack of guided flow and prompts in practice and in the field have been found to lead to high variability in the image capture and protocols employed in different screening settings around the world. The unique software and guided flow of the present invention, as described in detail below, enforces standardization and consistency in a highly user-friendly manner so that images that convey important diagnostic characteristics of tissue are captured and can be more reliably compared and assessed between doctors and patients.

In accordance with the present invention, an exemplary colposcopy instrument is controlled by a specific set of steps defined in software to follow a defined protocol for performing a colposcopy examination. The software is utilized to also control the features of an included camera so that consistent digital images are recorded. The integrated software prompts the medical personnel performing the colposcopy procedure to capture relevant images in an automated sequence that includes, for example, capturing a sequence of images after the application of the acetic acid to the cervix.

An associated user interface guides the individual performing the exam through a series of easy-to-understand screen prompts to capture specific, critical images during the exam. The process, once begun, is automated and does not require the individual performing the exam to make any decisions about whether or not to record a certain image. The relevant still images of the acetic acid uptake by the tissue (as well as perhaps a video recorded in an exemplary embodiment of the present invention), are displayed to the medical personnel at the end of the procedure, including images taken before, during, and after acetic acid application. The rate of acetic acid uptake by the cervix within a certain time interval can be an important characteristic to aid in diagnosing cervical pre-cancer. Images of the squamocolumnar junction (SCJ) may also be recorded, as well as an image after the application of Lugol's iodine.

Advantageously, the recorded image (and video) information may be uploaded from the device to a medical diagnosis platform accessible by networked clinicians worldwide. By providing a standardized procedure, the guided colposcopy procedure of the present invention provides more consistent results that are less susceptible to the skill level of the individual performing the exam, and ensures that all relevant information is collected during each examination.

An exemplary embodiment of the present invention takes the form of a method for carrying out a guided colposcopy procedure utilizing a combination of a digital camera and a computer-controlled colposcopy instrument including a display screen, where the method includes at least the steps of: (1) initiating the computer-controlled colposcopy instrument to display a plurality of selectable options associated with a set of defined steps in the guided colposcopy procedure including at least a step of performing an acetic acid uptake; (2) selecting values for each option of the plurality of selectable options presented on the display; (3) commanding the computer-controlled colposcopy instrument to activate the digital camera so as to present a digital image of a cervix region of interest (ROI) on the display; (4) presenting a set of timeline milestones as an overlay on the digital image, each milestone associated with an individual step of the set of defined steps in the guided colposcopy procedure; (5) prompting medical personnel performing the guided colposcopy procedure through each individual step, changing the visual display of each milestone as its associated step is completed; (6) collecting digital images of the cervix ROI as prompted by the computer-controlled colposcopy instrument; and (7) creating a final report of the colposcopy procedure in tangible form, the final report including at least a listing of selected options and a plurality of digital images of the cervix ROI captured during the procedure.

Other and further aspects and features of the present invention will become apparent during the course of the following discussion and by reference to the accompanying drawings.

BRIEF DESCRIPTION OF THE DRAWINGS

Referring now to the drawings.

DETAILED DESCRIPTION

FIGS. 1-17 present a series of screen shots that are displayed to the individual performing the examination (referred to hereinafter at times as "medical personnel"), guiding him/her through the process. In accordance with the principles of the present invention, the software-based guided colposcopy procedure is loaded into a portable computing device, such as a tablet, with touchscreen (or keyboard) controls that assist in making the process easy to follow for those with little training or experience. The computing device includes a display that not only provides graphical prompts to guide through the sequence of steps forming the procedure, but also displays the image of the cervix being examined as captured by an associated camera. An exemplary configuration of the components forming an embodiment of the automated colposcopy instrument will be discussed below, in association with FIGS. 18 and 19.

It is an advantage of the present invention that once an initial set of process parameters is selected (as discussed below in association with FIG. 4), the remainder of the process is automated and the digital images recorded during the examination are truly independent of the level of expertise of the individual performing the examination in as much as they are able to position the camera in front of the cervix.

Figure 1:
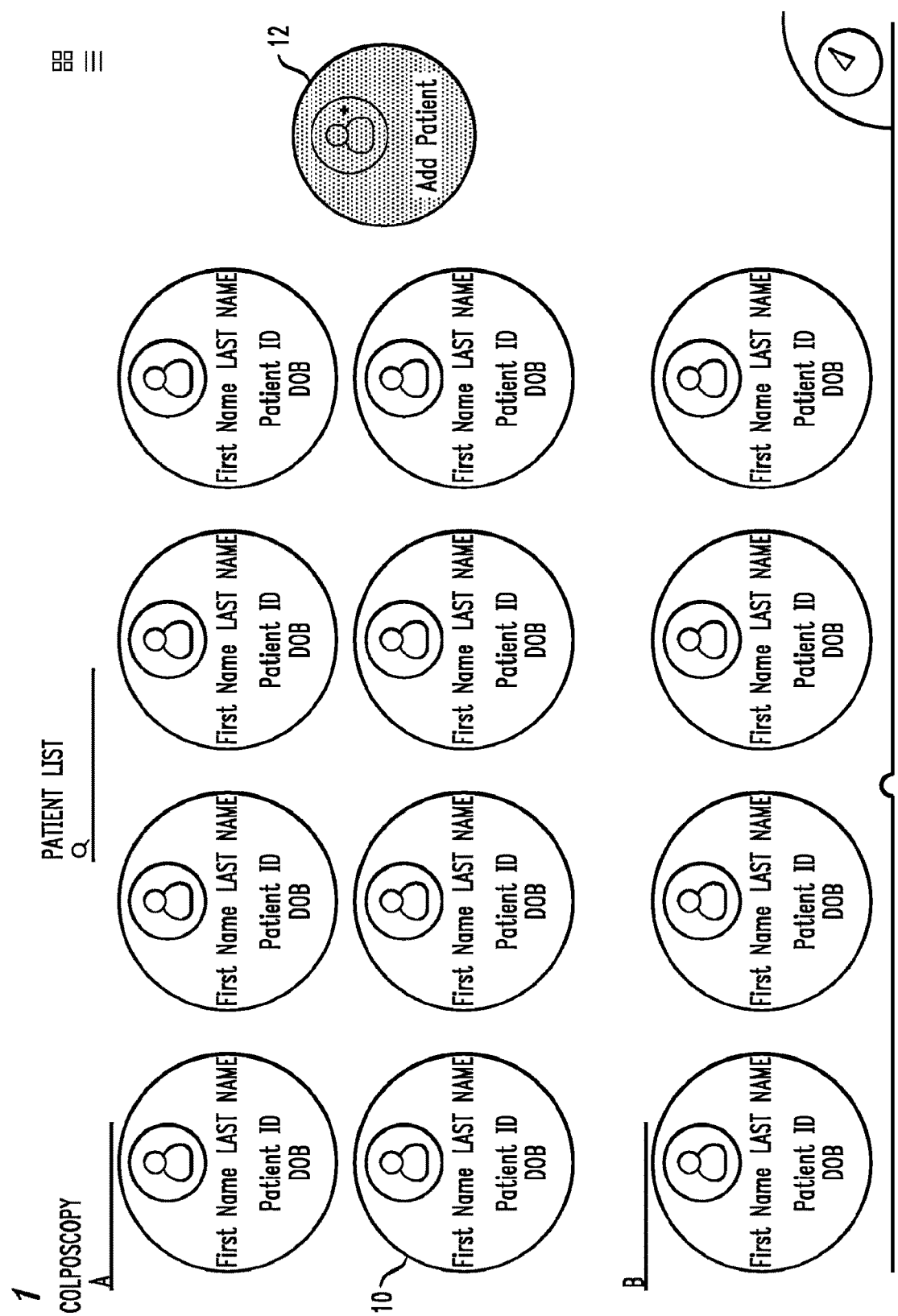
FIG. 1 depicts an initial screen that may be presented to medical personnel upon the initiation of a guided colposcopy procedure.
Figure 2:
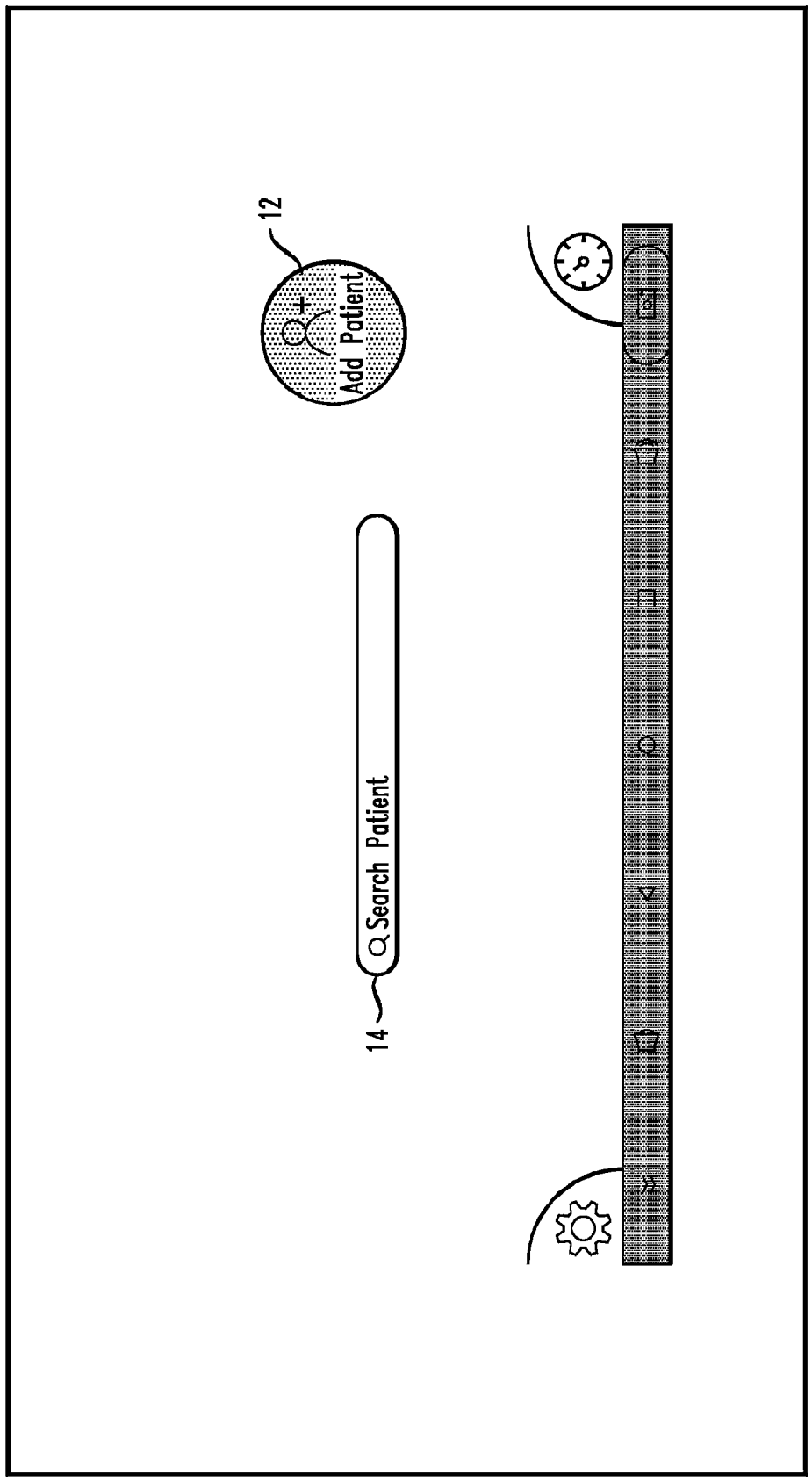
FIG. 2 illustrates an alternative initial graphic display that may be presented, with the understand that various other introductory screens may be presented at the beginning of the guided colposcopy procedure.

FIG. 1 shows an initial screen that may be displayed upon the medical personnel logging in and entering the guided program for enabling an automated colposcopy procedure. The screen displays an alphabetical listing of all registered patients (with the ability, obviously, to scroll through to show listings for last names A through Z). For the purposes of explanation, it is presumed that the medical personnel performing the guided colposcopy procedure selects the patient identified by numeral 10. Alternatively, if the current patient's information cannot be found, the medical personnel activates the "add patient" button 12, which then presents a patient "intake" screen where the details of the individual can be entered. FIG. 2 depicts an alternative initial screen that may be used, where instead of being presented with a complete listing of existing patients, the medical personnel enters identification information (e.g., patient name, patient ID number, or the like) in a search bar 14. Again, if not found, "add patient" button 12 may be activated to allow for new patient information to be added to the database associated with the system. The configurations shown in FIGS. 1 and 2 are considered to be exemplary only, and it is to be understood that various other visualizations may be used upon an authenticated user logging into the software-guided colposcopy procedure.

Figure 3:
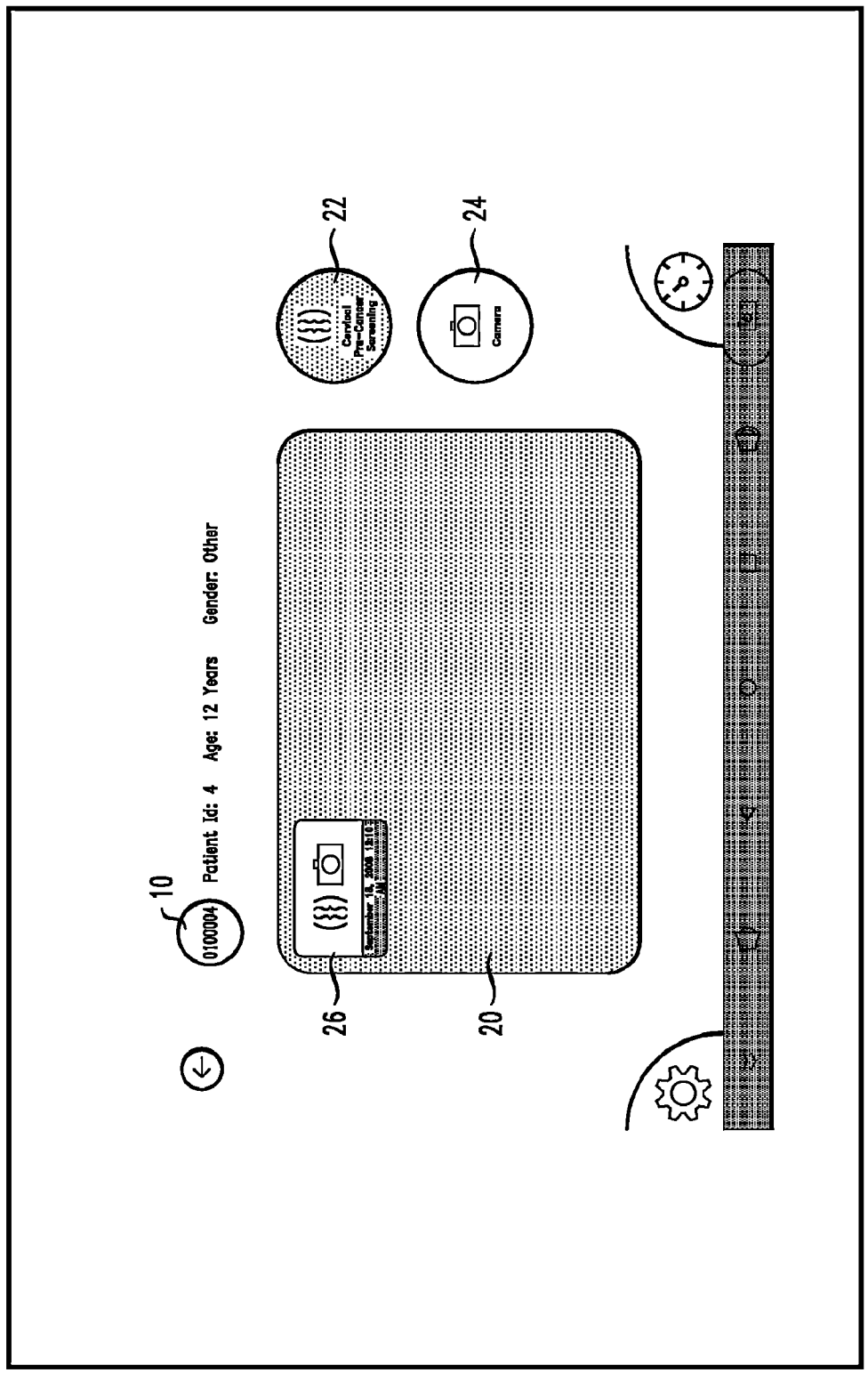
FIG. 3 shows one example of an initial patient screen that appears upon selection of the proper individual for the current procedure.

FIG. 3 shows one example of an initial patient screen that appears upon selection of a particular individual. In this specific configuration, the display includes a screen area 20 that may illustrate, for example, prior results from a previous examination. This is illustrated as an icon 26 within screen area 20. In this case, icon 26 is associated with an electronic file of a previous examination for review by the medical personnel before continuing with the procedure. Other patient history may be displayed as well. Presuming that all of the displayed information is correct, the medical personnel then activates the actual colposcopy process using button 22, which may be identified by a label such as "begin colposcopic examination". It is to be noted that the phrases "colposcopic examination", "cervical pre-cancer screening" and "colposcopy procedure" may be used interchangeably for the purposes of explaining the principles of the present invention.

In the particular configuration as shown in FIG. 3, there is another option available to the medical personnel, shown here as a "camera" button 24. As will be discussed in more detail below, the instrumentation used to perform the procedure includes a camera that takes pictures (and perhaps videos) of the procedure. If the medical personnel does not want to perform the entire colposcopy procedure, but only wants to take a few pictures (perhaps as part of a follow-up visit), the procedure itself may be bypassed and the automated program instructed to move into a flow that allows for any desired number of digital images to be recorded.

Figure 4:
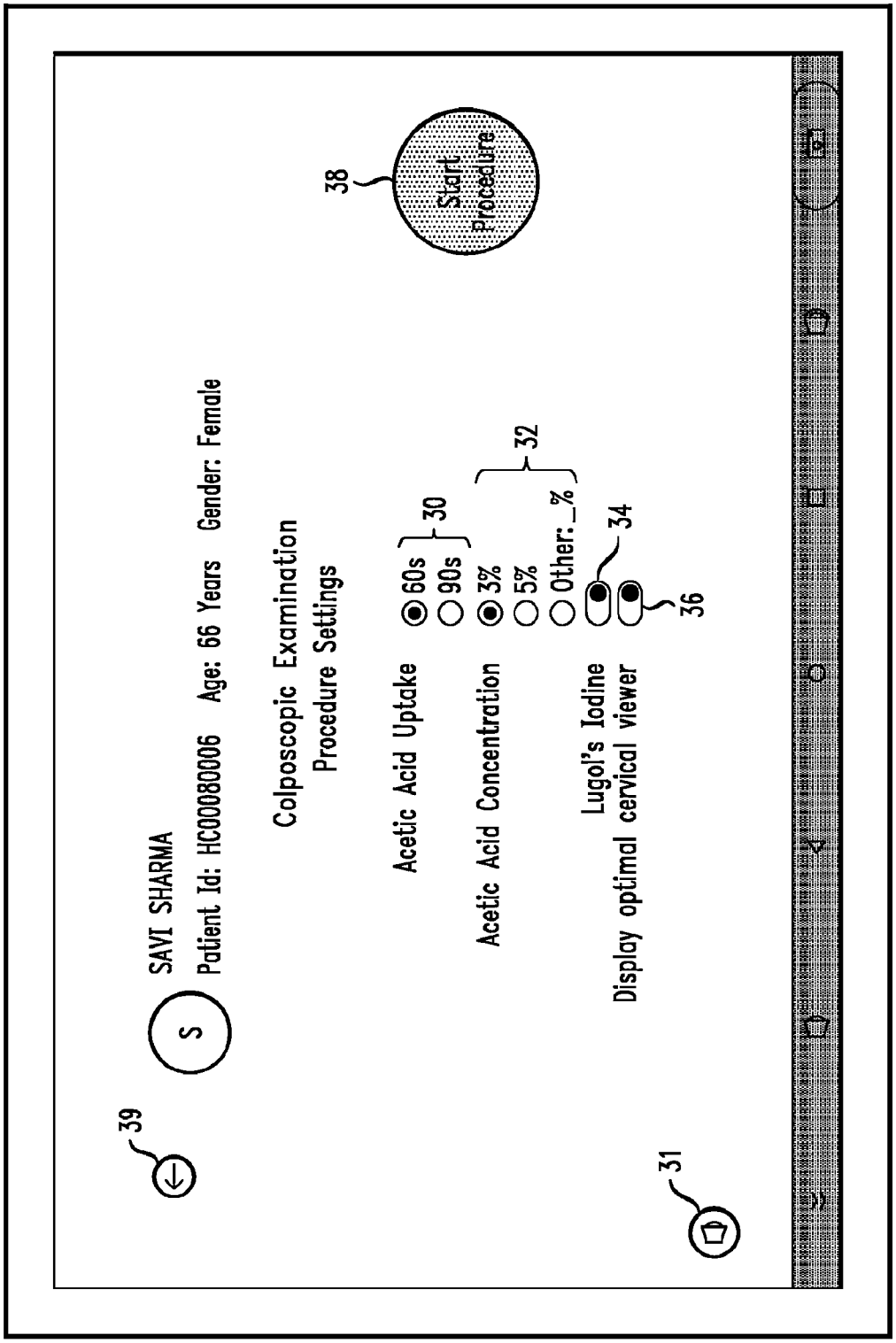
FIG. 4 is an exemplary screen shot showing a set of selectable options, controllable by the medical personnel performing the procedure, including the selection of acetic acid uptake interval (and specific acid concentration)

For the sake of discussion, it will be presumed that the medical personnel has activated button 22 to initiate the guided colposcopy procedure. At this point, the screen shot as shown in FIG. 4 is presented to the medical personnel. This initial screen presents the only selectable "options" available to the medical personnel, helping to maintain consistency and standardization in the colposcopy procedure regardless of the specific individual performing the procedure (as well as the skill/level of expertise of the individual). One exemplary set of such options may include: (1) the ability to use audio prompts; (2) selection of a specific image capture interval for acetic acid uptake (as well as the selected acetic acid concentration); (3) whether or not to include a test using Lugol's iodine in the procedure; and (4) whether or not to activate an image viewer system that guides the positioning of the camera properly in front of the cervix.

The ability to use audio prompts to guide the medical personnel through the colposcopy procedure (shown as option 31 in FIG. 4) is considered to be particularly advantageous for inexperienced personnel and is obviously presented in the preferred language of the individual performing the procedure. For those at a higher skill level, the audio prompts may be turned "off", by control of the radio button for option 31. Additionally, the audio capabilities may be used to record "spoken" notes dictated by the medical personnel as the procedure is taking place. Included software may be used to perform speech-to-text conversion of the spoken notes into written comments that form part of the final report of the procedure.

The image capture interval selection (shown as selectable option 30 in FIG. 4) is associated with the duration of time during which the acetic acid uptake on the cervix will be recorded. In the particular configuration of the present invention as shown FIG. 4, selectable option 30 allows for only two choices, the first capturing a set of images during a 60-second interval and the second capturing a set of images during a 90-second time interval. In either case, a video may also be recorded of the acetic acid uptake for the complete time interval within which the still images are recorded. It is presumed that if relatively new or inexperienced medical personnel is performing the procedure, she/he will be instructed as to which option to select based on a protocol established by the organization overseeing the colposcopy procedure, or as time allows for the patient exam.

Another aspect of the acetic acid uptake procedure is selecting a proper acid concentration, where it is known that different concentrations are better suited for specific situations. In most cases, either a 3% or 5% concentration is used, and these are illustrated as selectable radio buttons with option 32. For those instances where the medical personnel performing the procedure is utilizing a specialized concentration, that possibility is also shown, with the ability for the individual to enter the specific concentration being used. Advantageously, all of the entered information is retained as part of the record of the colposcopy procedure, so at a later point in time anyone else reviewing the patient record will know that this particular acetic acid uptake utilized this "specialized" concentration.

Also shown in FIG. 4 is a selectable option 34, defined as "Lugol's Iodine" (with a yes/no choice to make). Lugol's iodine is a second test that may be performed by swabbing the cervix with iodine to provide an additional visual contrast between abnormal and normal tissue. There are a variety of factors associated with whether or not this additional test is warranted for use, including the availability of Lugol's iodine in the medical setting. Again, it is presumed that if an inexperienced individual is performing the colposcopy procedure, there will be a pre-defined protocol instructing that person with respect to whether or not to include this second test.

The final selectable option 36 is defined as "display optimal cervical viewer" and when selected by the medical personnel, a static square box will be displayed in the center of the visual field. Thereafter, the medical personnel can use the camera controls (described in detail below) so that the cervix being viewed is located within this box. Alternatively, the software controlling the guided process may include the AI capability to automatically locate the boundaries of the cervix and control the camera to optimize its position such that the cervix image is within the guide box. The use of the cervix guide box, as discussed below in association with FIG. 10, helps to ensure that the images captured during the procedure by the associated camera are focused and of an acceptable quality for later review by all personnel having access to the final report from the procedure.

While in a relatively basic implementation the guided colposcopy procedure of the present invention may define a set of default camera settings, an embodiment of the present invention may also incorporate the capability to control camera settings, the latter option being a useful tool for more highly-skilled medical personnel.

Figure 5:
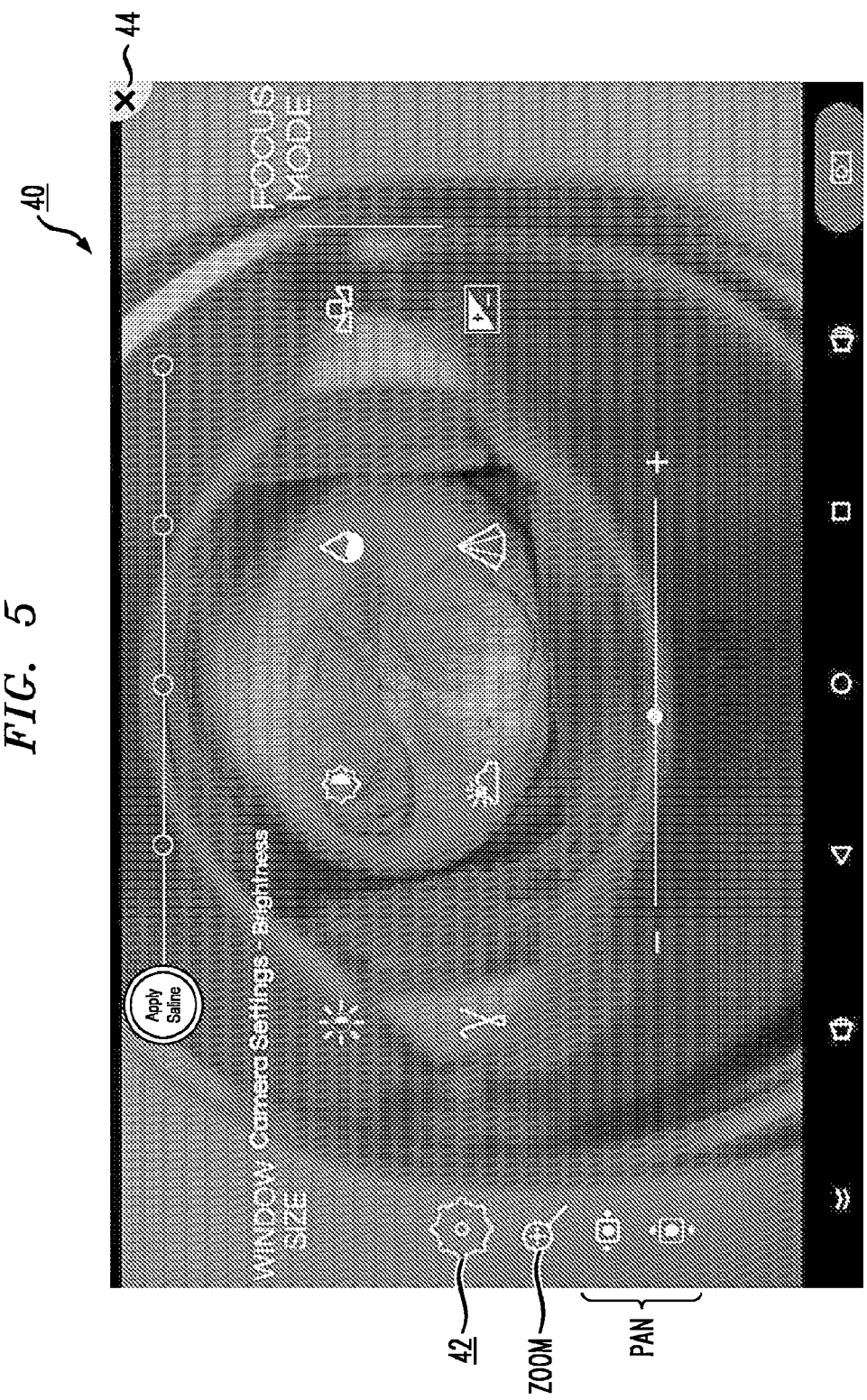
FIG. 5 is a screen shot depicting an exemplary set of camera settings that may be adjustable by the medical personnel performing the procedure (or alternatively automatically controlled by the guided colposcopy process itself)

FIG. 5 is a screen shot of an exemplary set of camera settings 42 that may be controlled by the medical personnel at any point in time during colposcopy procedure. A "reset" option is included with the camera settings and may be activated to return the camera's operation to the "default" settings. Shown as camera settings 42, the medical personnel may adjust the horizontal and vertical positioning of the camera, as well as zoom "in" or "out", as need be. If such introductory camera adjustments are not required, the medical personnel can merely exit the page (see, the "x" 44 at the corner of the FIG. 5 screen shot).

Returning now to the particular illustration of FIG. 4, in this exemplary procedure, the medical personnel has set options 30, 31, 32, 34 and 36 to have the following selections: (1) the audio prompts are to be played while the procedure is being performed; (2) the 60-second acetic acid uptake interval is to be used with the application of 3% acetic acid, and (3) a Lugol's iodine test is to be included.

As shown in FIG. 4, the actual procedure begins by having the medical personnel activate radio button 38, "start procedure". Also shown in the screen shot of FIG. 4 is an "exit" button 39. If for some reason or other the colposcopy procedure needs to be paused or cancelled, the individual can use exit button 39 to return to the main menu.

Figure 6:
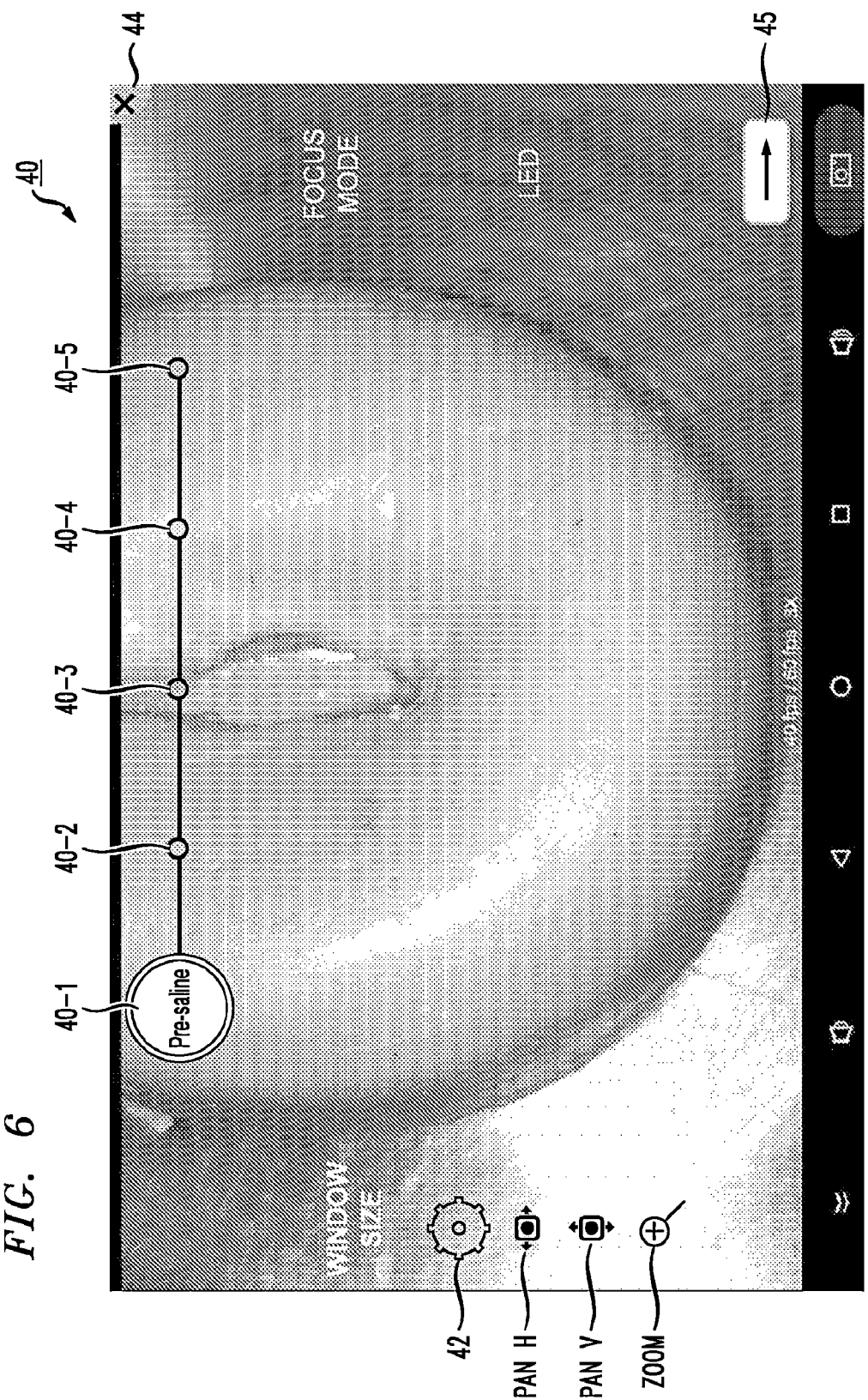
FIG. 6 is a screen shot of a display associated with an initial step in an exemplary guided colposcopy process.

Presuming that the actual guided colposcopy procedure has been initiated, the camera included in the instrumentation is activated, with the subject cervix being imaged and displayed on the device screen being used by the medical personnel to guide him/her through the process. As shown in FIG. 6, the image of the cervix is overlaid with a set of prompts for guiding the medical personnel through the colposcopy procedure. In this case, the prompts are displayed as individual milestones along a progression timeline 40. The individual milestone of a current step in the procedure is shown in expanded form and includes a label identifying that particular step. Upon completion of a step, the milestone is again displayed in its original size and changed in appearance to indicate that it has been performed. For example, "open circles" may be used to indicate those steps remaining in the procedure and "closed circles" may be used to indicate those steps that are completed. In most cases, the medical personnel will be instructed to "tap" or "click" on the active milestone to first initiate the associated step, and may utilize a second "tap" or "click" used to indicate that the step has been completed (which will then move the guided colposcopy procedure to display the following step). Instead of activating the milestone a second time, a separate "next" icon 45 may appear on the screen, with the medical personnel then tapping or clicking on next icon 45 to proceed to the next step in the guided colposcopy procedure. As an alternative to the need to tap or click on the display itself, the guided colposcopy procedure of the present invention may also be responsive to audio commands from the medical personnel to proceed to the next milestone.

Figure 7:
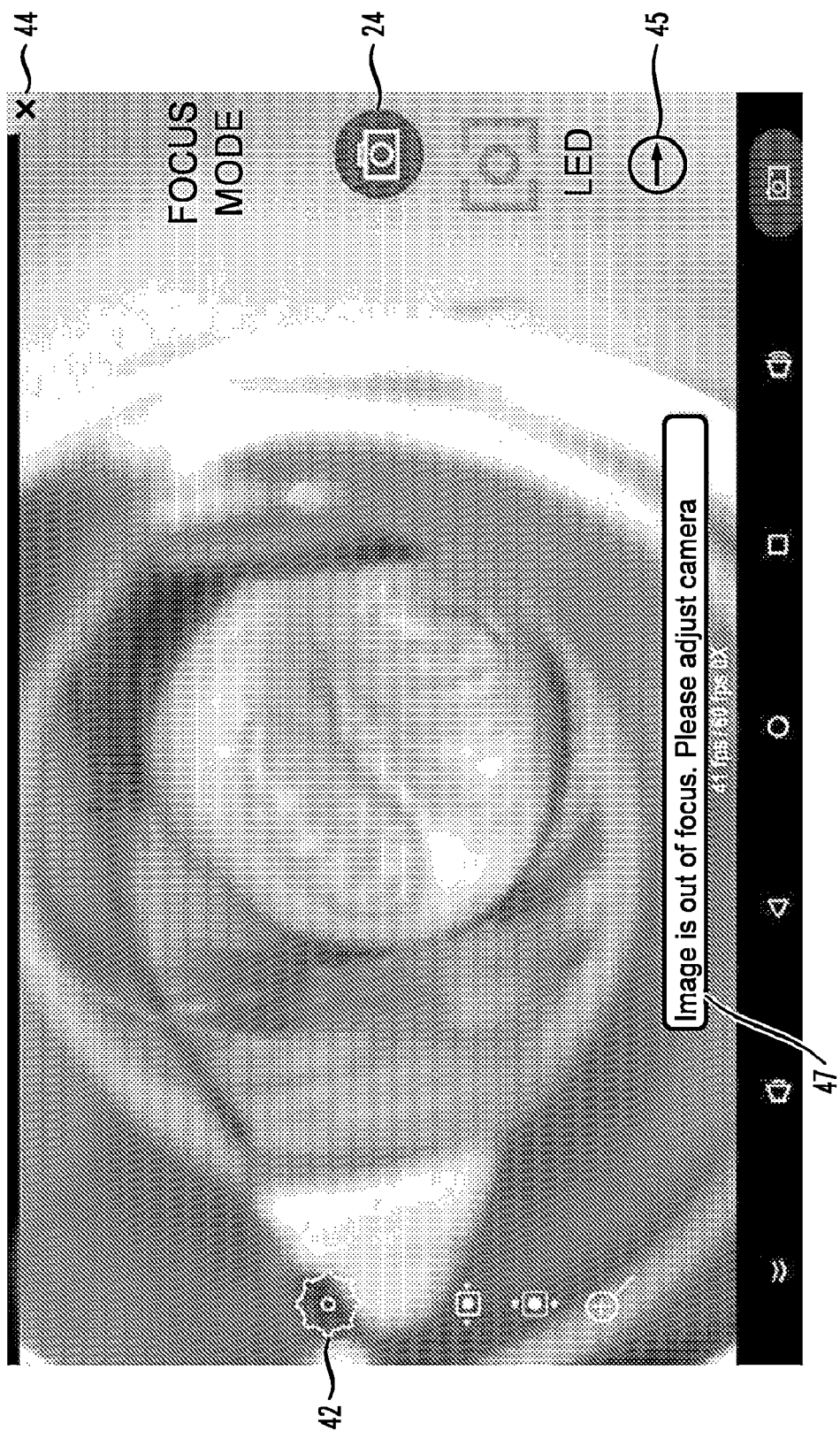
FIG. 7 depicts a screen shot of an exemplary "image check" step that may be included to confirm camera settings prior to the initiation of image capture in accordance with the principles of the present invention.

Continuing with reference to the screen shot of the guided colposcopy process as shown in FIG. 6, a first milestone 40-1 is indicated as a "pre-saline" step. As a preliminary action, this step is used as an "image quality" check, where both the focus and lighting conditions on the cervix will be automatically assessed, based on software parameters used to judge the quality of the image. FIG. 7 is a screen shot illustrating an exemplary result of this image quality check. If the image appears to be too blurry (as is the case in the exemplary screen shot of FIG. 7), or if the lighting is too dark/bright on the display, a message 47 will appear on the display, prompting the medical personnel to adjust the camera focus or lighting, accordingly. This pre-procedure check of the image quality ensures that clear, high-quality images are captured during the procedure. While not expressly discussed below, this image quality check may be performed at each milestone to maintain the quality of the captured images under different circumstances. Once the camera conditions are satisfactory, the medical personnel can use any of the methods described above to advance the guided colposcopy procedure.

Figure 8:
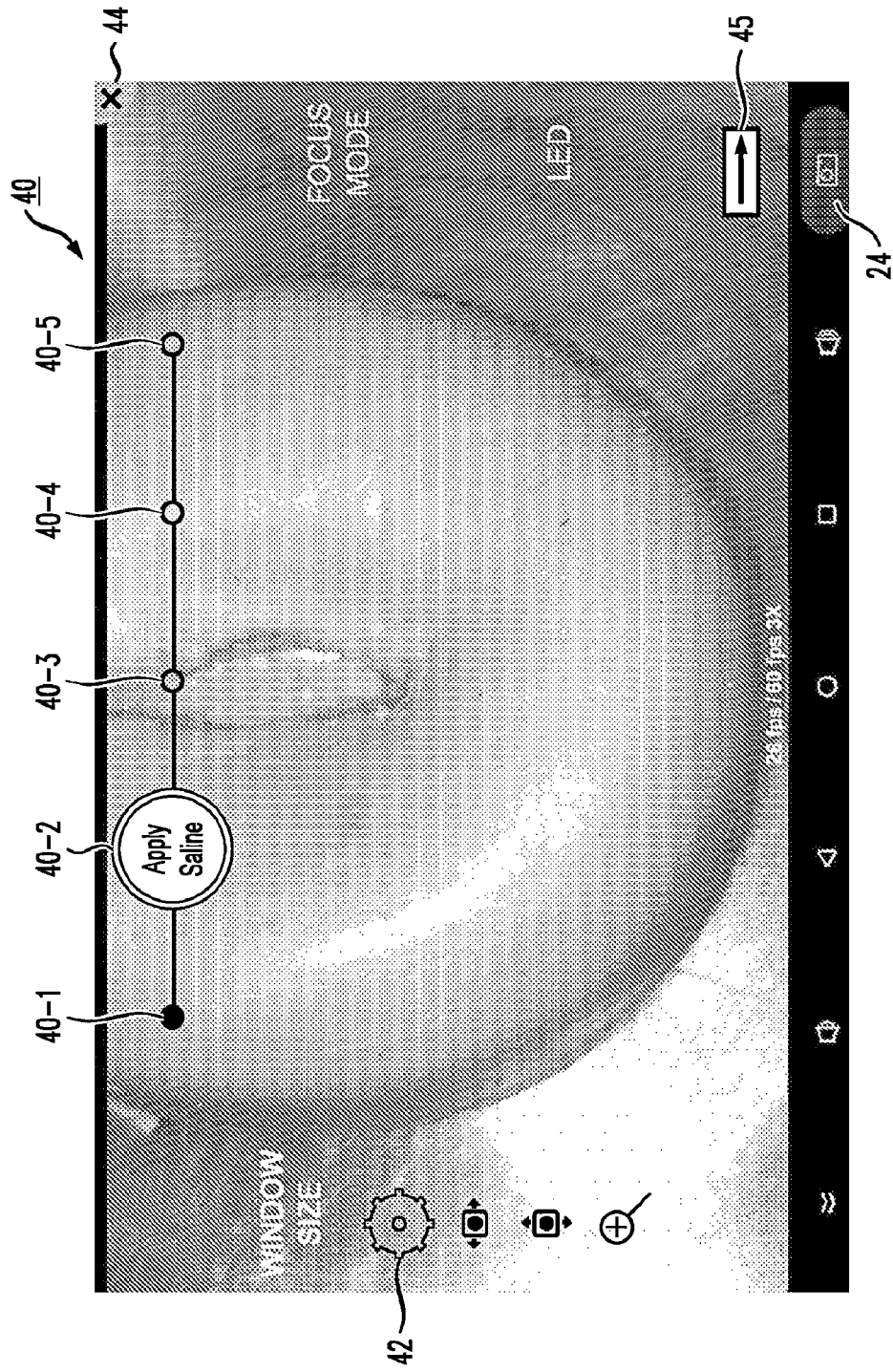
FIG. 8 is a screen shot of a display associated with a next step in the guided colposcopy procedure, denoted "apply saline"

The next step in the process is shown in the screen shot of FIG. 8. In particular, milestone 40-2 of progression timeline 40 is now shown as enlarged, prompting the medical personnel to now "apply saline" to the cervix. In accordance with the guided colposcopy procedure, milestone 40-1 is now shown as a closed circle, providing visual confirmation to the medical personnel that this step has been completed. Once milestone 40-2 is activated, a camera icon 43 appears on the display, allowing the medical personnel to capture one or more images of this step in the guided colposcopy procedure. Indeed, if the audio prompts are enabled, the personnel may be instructed to capture at least one image before proceeding to the next step. Once the images have been captured, the medical personnel may either "tap" or "click" on milestone 40-2 to indicate the completion of the saline application step in the guided colposcopy procedure. It is to be understood that instead of again activating the milestones, the "next" arrow 45 at the bottom of the page may be used to advance the process, a technique well-known and familiar to individuals trained in computer-based tasks. Indeed, "next" arrow 45 appears on each screen through the guided procedure and may be used to advance through the individual steps of the procedure.

Figure 9:
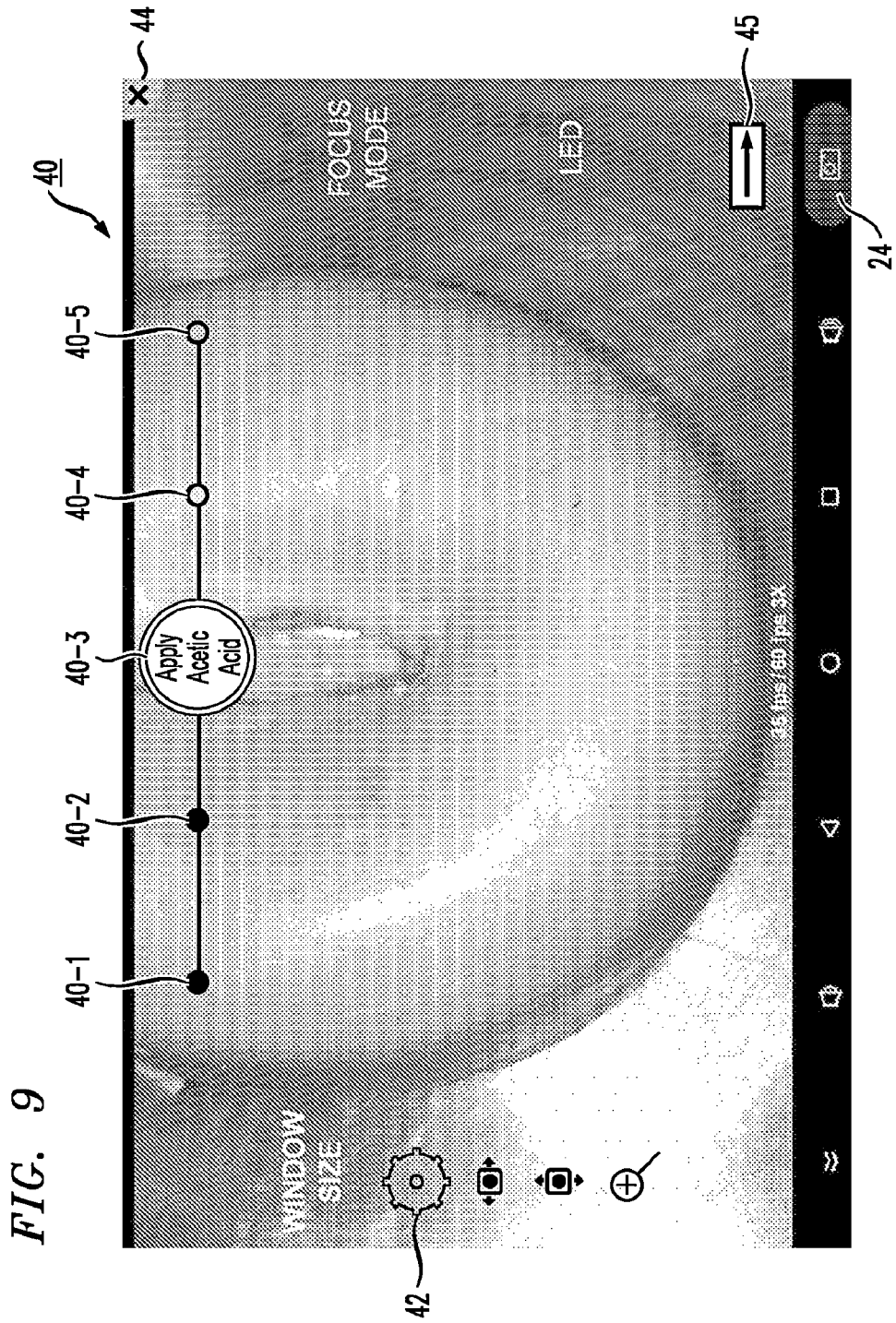
FIG. 9 includes a screen shot next displayed by the guided colposcopy procedure, prompting the medical personnel to apply the acetic acid and begin the recording of images (and/or video) at set times during the pre-defined uptake interval.

Reference is now made to FIG. 9, which contains a screen shot of a following step in the guided colposcopy procedure. As shown, the medical personnel will now be prompted (shown as milestone 40-3) to swab the cervix with the selected concentration of acetic acid solution. Once activated, milestone 40-3 may then change the displayed information to show the instruction "start uptake" (this prompt, like others, may include different texts to guide the procedure; for example, a phrase such as "prep done" may be displayed). Thus, once the cervix has been swabbed, the medical personnel again taps/clicks milestone 40-3 to activate the acetic acid uptake portion of the procedure.

Figure 10:
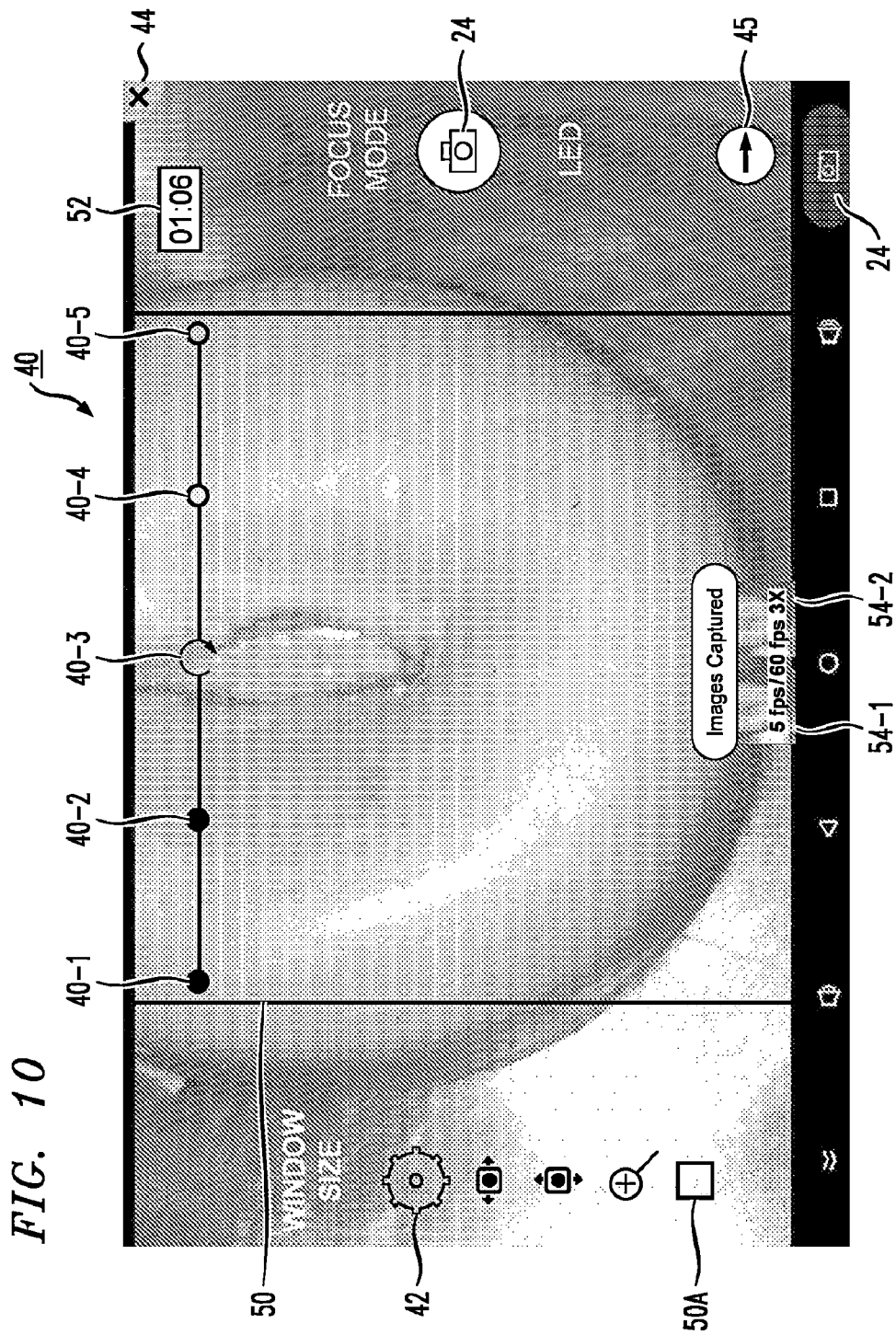
FIG. 10 illustrates the on-going capture of digital images during the acetic acid uptake step of the guided colposcopy procedure.

FIG. 10 shows an exemplary screen shot of the progression of the acetic acid uptake step in the colposcopy procedure. As mentioned above, a guide box 50 may be used (if selected by "viewer" button 36 in the initial selection settings) to overlay the camera image and ensure that the camera remains centered in the "region of interest" (ROI). The medical personnel can use the camera movement controls (if available) to ensure the positioning of the ROI within guide box 50 (and may also turn "off" guide box 50 once the desired centering is achieved). It is contemplated that in an alternative embodiment of the software-guided process of the present invention, an algorithmic process may be used to control the camera settings so as to automatically perform the centering of the ROI within guide box 50 (a particularly helpful feature for less-experienced medical personnel). In some embodiments, the screen shot may include a guide box radio button 50A, allowing the medical personnel to toggle between displaying/hiding guide box 50. A timer 52 is also displayed during the acetic acid uptake to provide a timestamp for the captured images. Thumbnails 54 of the captured images are also displayed in real time as the uptake is progressing, where a pair of thumbnails 54-1 and 54-2 is shown in FIG. 9. It is also possible to indicate the on-going nature of the uptake interval by displaying milestone 40-3 with a rotating boundary, as shown in FIG. 10.

Figure 11:
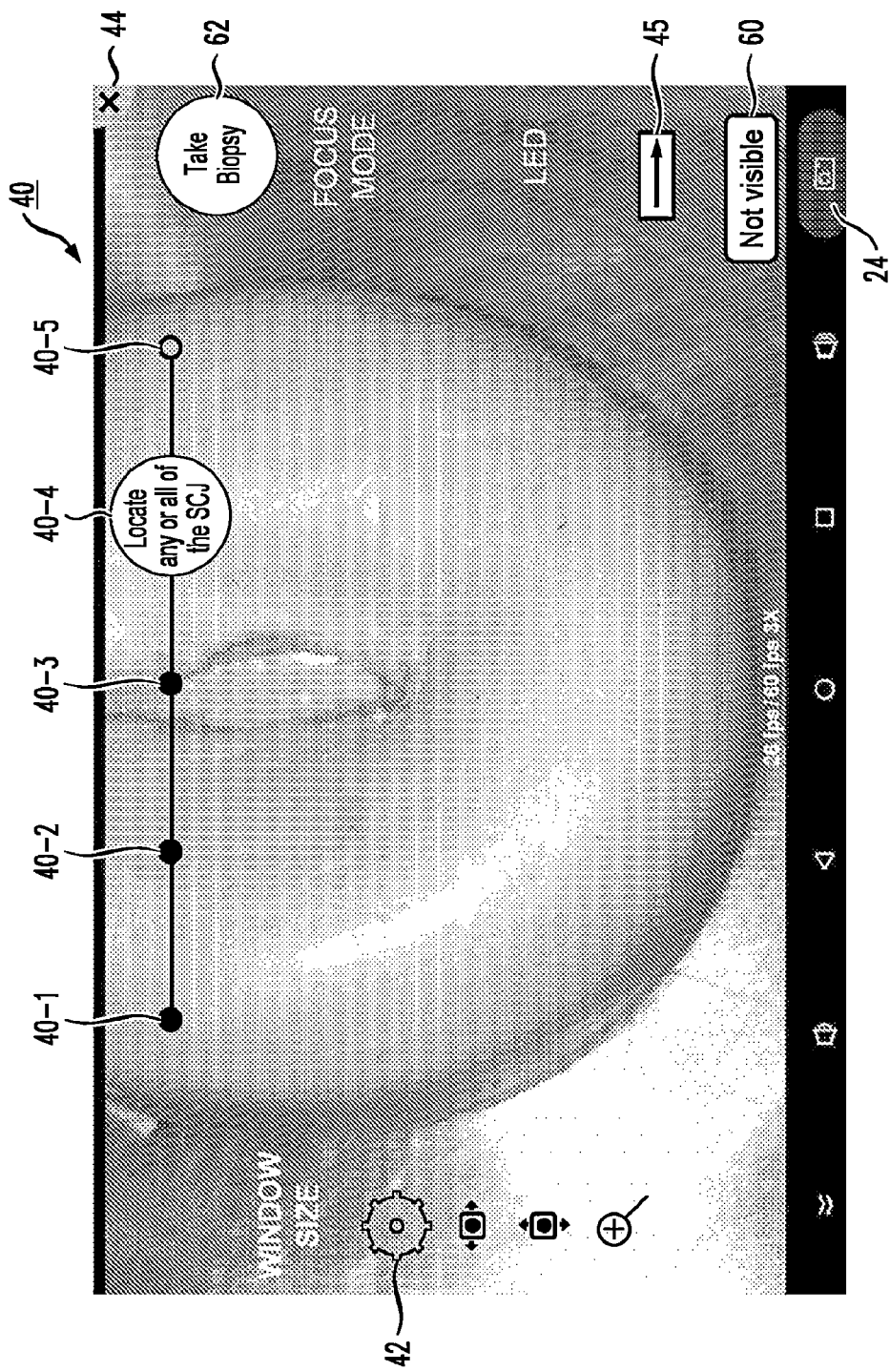
FIG. 11 is a screen shot of the guide colposcopy procedure at the completion of the acetic acid uptake step, prompting the medical personnel to locate the SCJ.

FIG. 11 is a screen shot of a following step in the colposcopy procedure upon completion of the acetic acid uptake process. At this point, the medical personnel is prompted to locate the squamo-columnar junction (SCJ) (milestone 40-4) and record a digital image. If the medical personnel is unable to identify the SCJ in the cervix, s/he is prompted to activate button 60, which is associated with "not visible", flagging this problem with viewing the SCJ and noting it as part of the patient's record related to this colposcopy procedure. It is contemplated that various other embodiments and aspects of the present invention include the capability to apply artificial intelligence (AI) techniques to the various recorded images to assist in finding the location of the SCJ.

Figure 12:
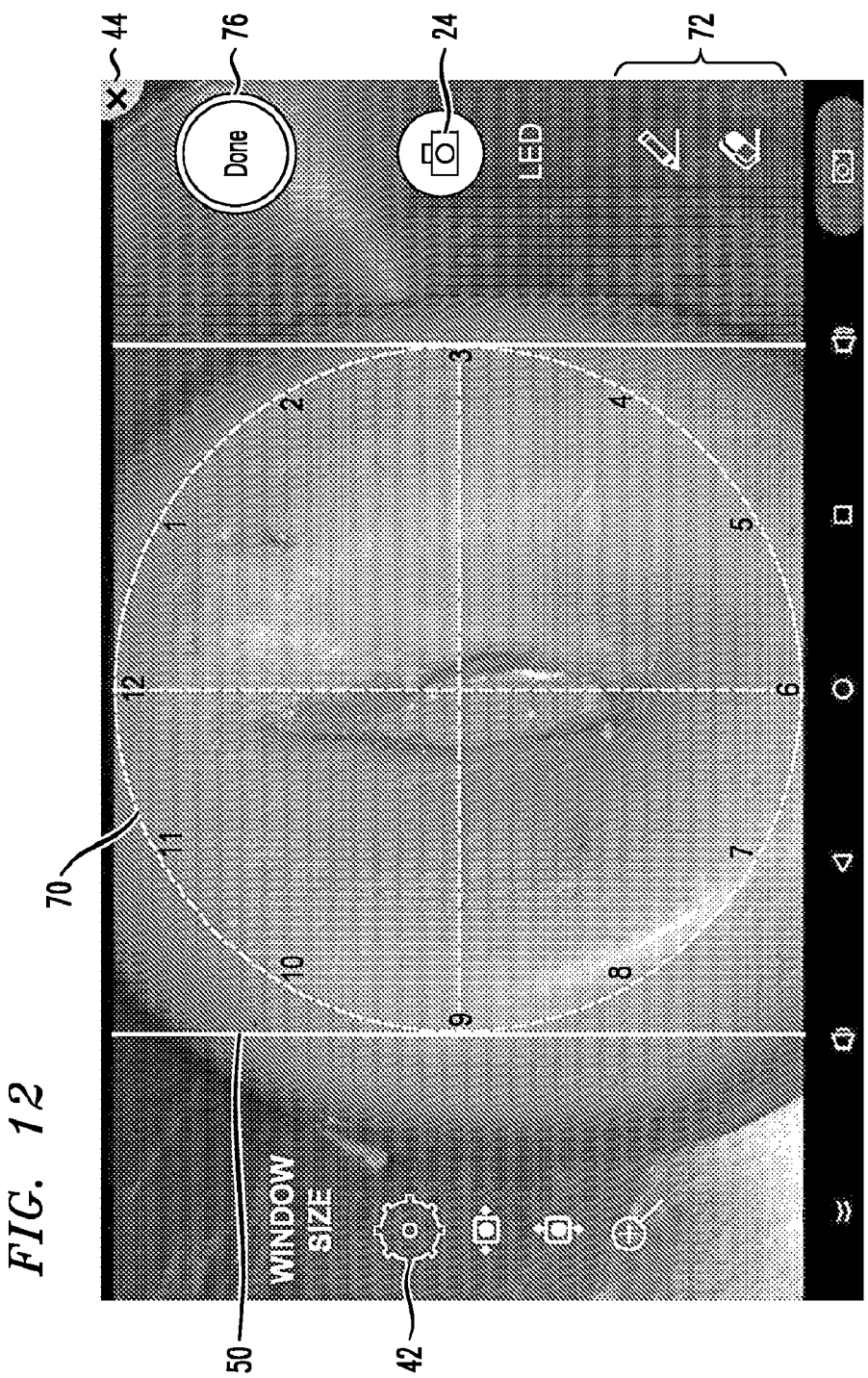
FIG. 12 contains a screen shot associated with an optional biopsy procedure that may be included within the guided colposcopy procedure, under the initiation and control of the medical personnel.

At any point in the procedure after the application of acetic acid, the medical personnel can elect to perform a biopsy (shown as the "take biopsy" selection radio button 62 in the screen shot of FIG. 11). Once activated, the presented image of the cervix is overlaid with a clock 70 (or other suitable location grid), as shown in the screen shot of FIG. 12. An on-screen editing pen 72 may be used to mark the location(s) of the biopsy on clock 70, with a digital image record of the biopsy location provided via activation of camera icon 24. This information is stored as part of the patient record and is useful as a reference for later access to show where the biopsies were taken from, as well as for treatment of a malignant lesion. Once the biopsy has been completed, the medical personnel is able to return to the guided colposcopy procedure by activating "done" button 76 as shown in FIG. 12. In certain embodiments of the present invention, the software utilized to guide the colposcopy procedure may incorporate specialized AI to assist in determining optimal location(s) for taking the biopsy sample.

Figure 13:
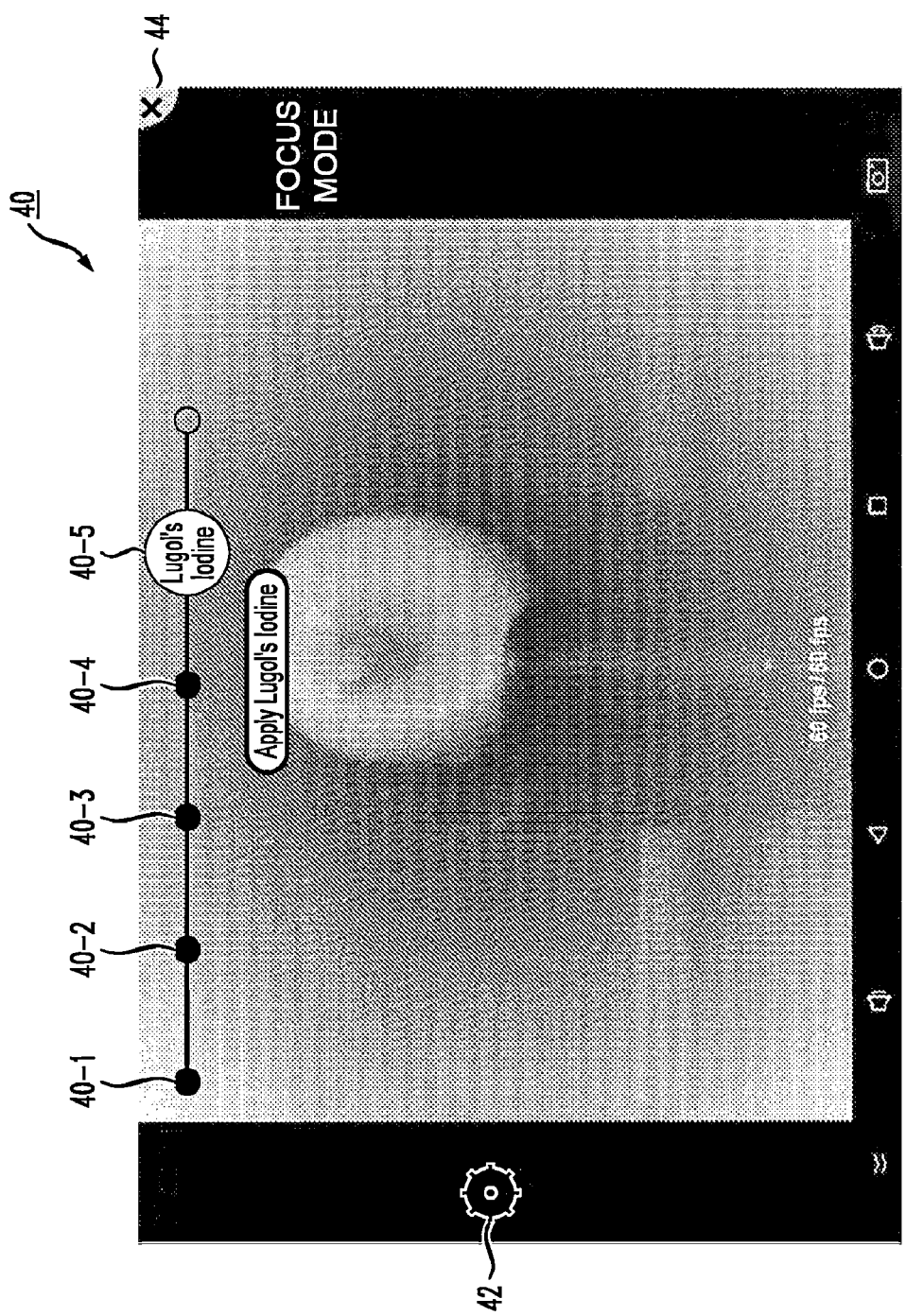
FIG. 13 is an exemplary screen shot of a following milestone along the guided colposcopy procedure, prompting the medical personnel to apply Lugol's iodine (if this step had been "selected" to be included in the procedure)
Figure 14:
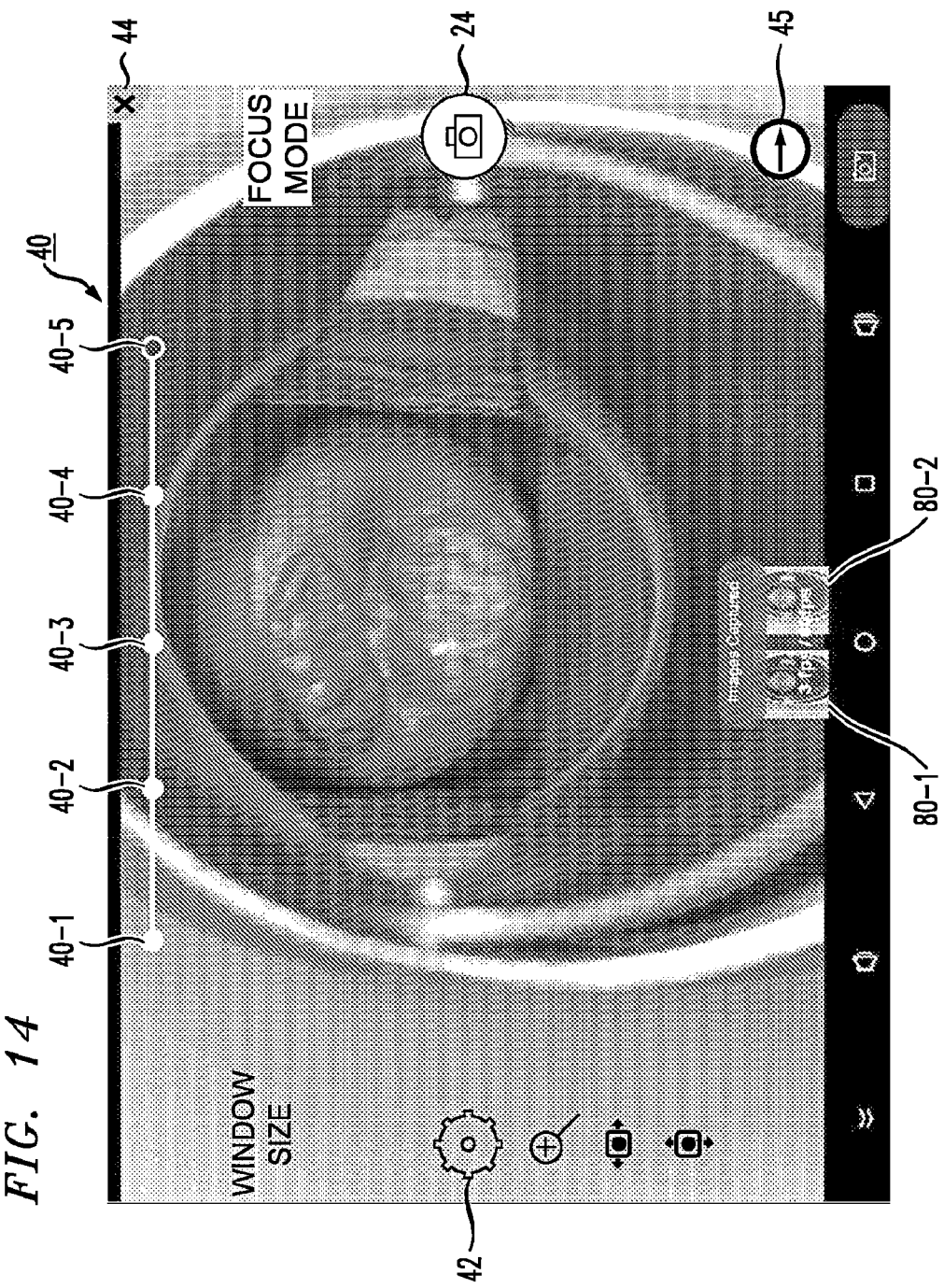
FIG. 14 is a screen shot illustrating the procedure subsequent to the application of the Lugol's iodine, which includes the capture of digital images under different camera settings (including different-colored filters)

It is to be recalled from the discussion associated with the screen shot of FIG. 4 that when making the choices for selectable options (30, 31, 32 and 34), the medical personnel in this case indicated that a Lugol's iodine test was to be included (i.e., selectable option 34 marked as "yes"). The guided colposcopy procedure of the present invention thus configures progression timeline 40 to include a milestone 40-5 for this step. Reference is made to FIG. 13, which shows an enlarged milestone 40-5, with language prompting the medical personnel to apply the Lugol's iodine. Once the Lugol's iodine has been applied, the medical personnel taps button 40-5 to bring up camera icon 24 on the display, as shown in FIG. 14. Images may then be captured by the included camera (perhaps under different lighting conditions-white light, green filter, etc.), with the images shown as thumbnails 80-1, 80-2 on the screen shot of FIG. 14. The iodine will be absorbed by normal tissue and thus provide further visual differentiation between normal and abnormal tissue.

Figure 15:
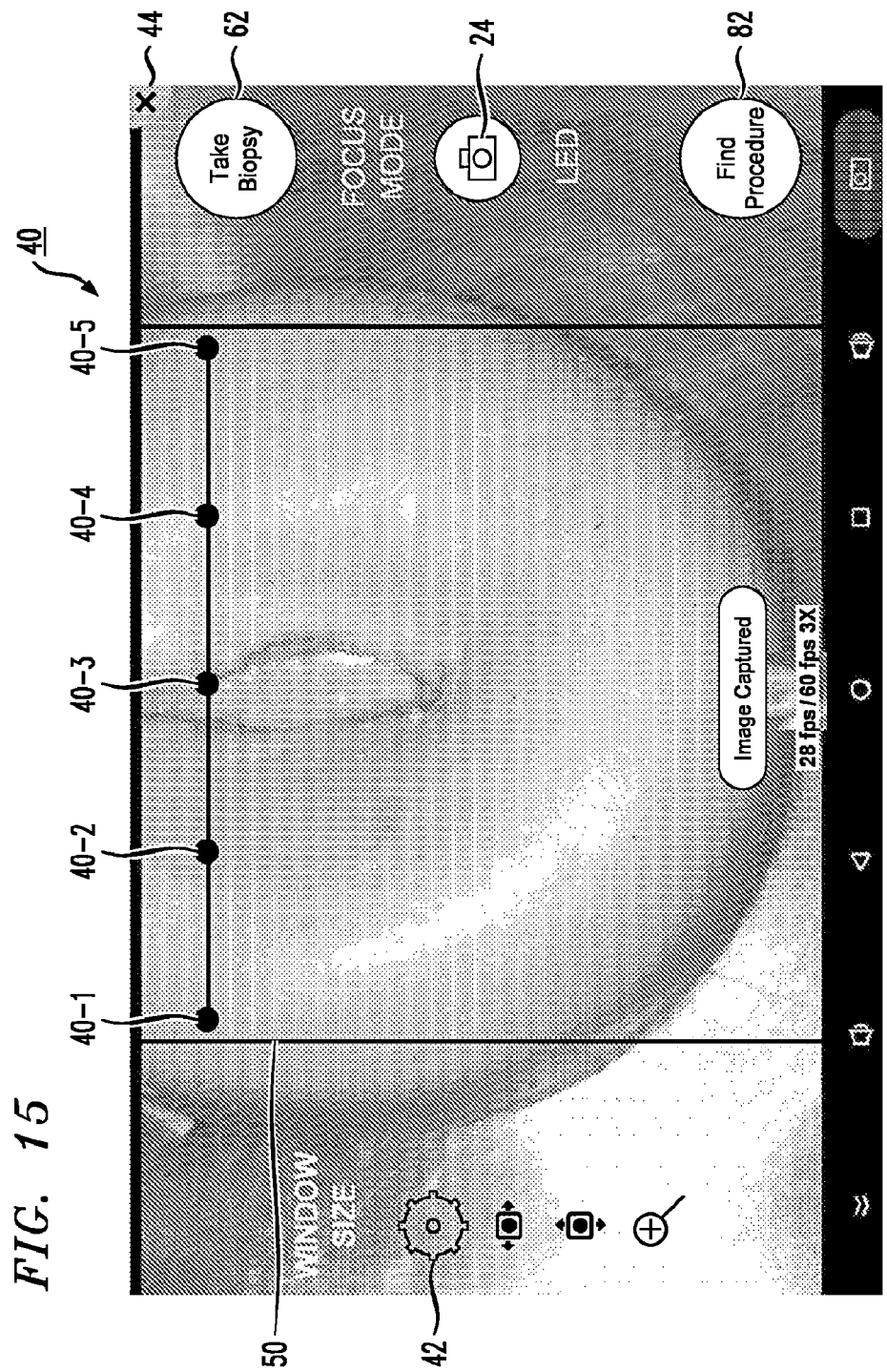
FIG. 15 is a screen shot depicting the completion of the guided colposcopy procedure, showing all of the milestones as completed steps in the procedure and including a prompt for moving on to the step of preparing a final report.

At the completion of milestone 40-5, the medical personnel is prompted to tap "next" button 45 (or again tap/click milestone 40-5), progressing to the next screen shot of the guided colposcopy procedure, as shown in FIG. 15. Inasmuch as each step in the procedure has now been completed, all of the milestones along progression timeline 40 are now displayed as closed circles. Camera icon 24 remains active, in the event that the medical personnel wishes to capture some additional images for the patient record. Also, if a biopsy has not yet been performed, the "take biopsy" radio button 62 will continue to appear as an available option.

Figure 16:
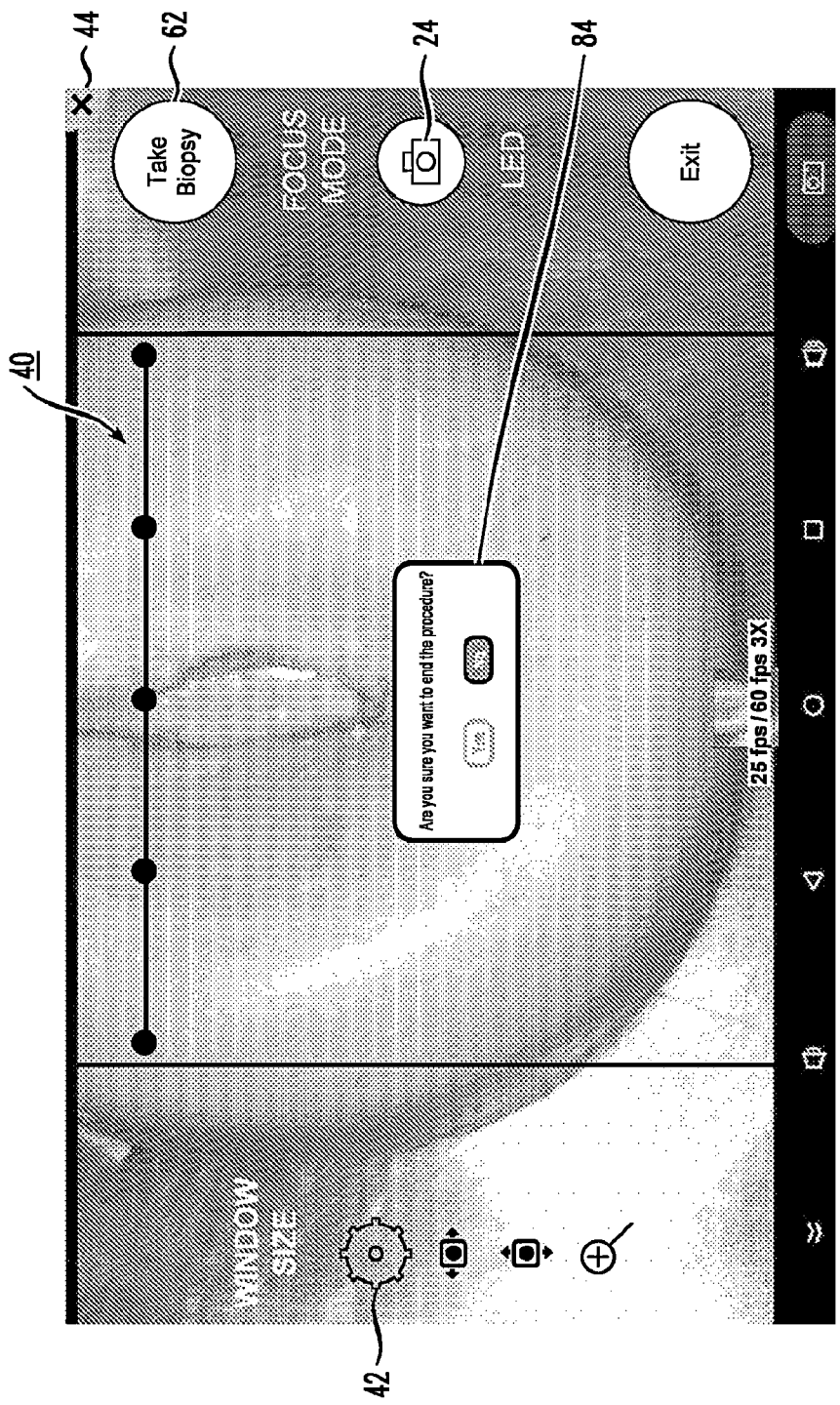
FIG. 16 illustrates an option screen that may be displayed requesting the medical personnel to confirm the request to "end" the procedure.
Figure 17:
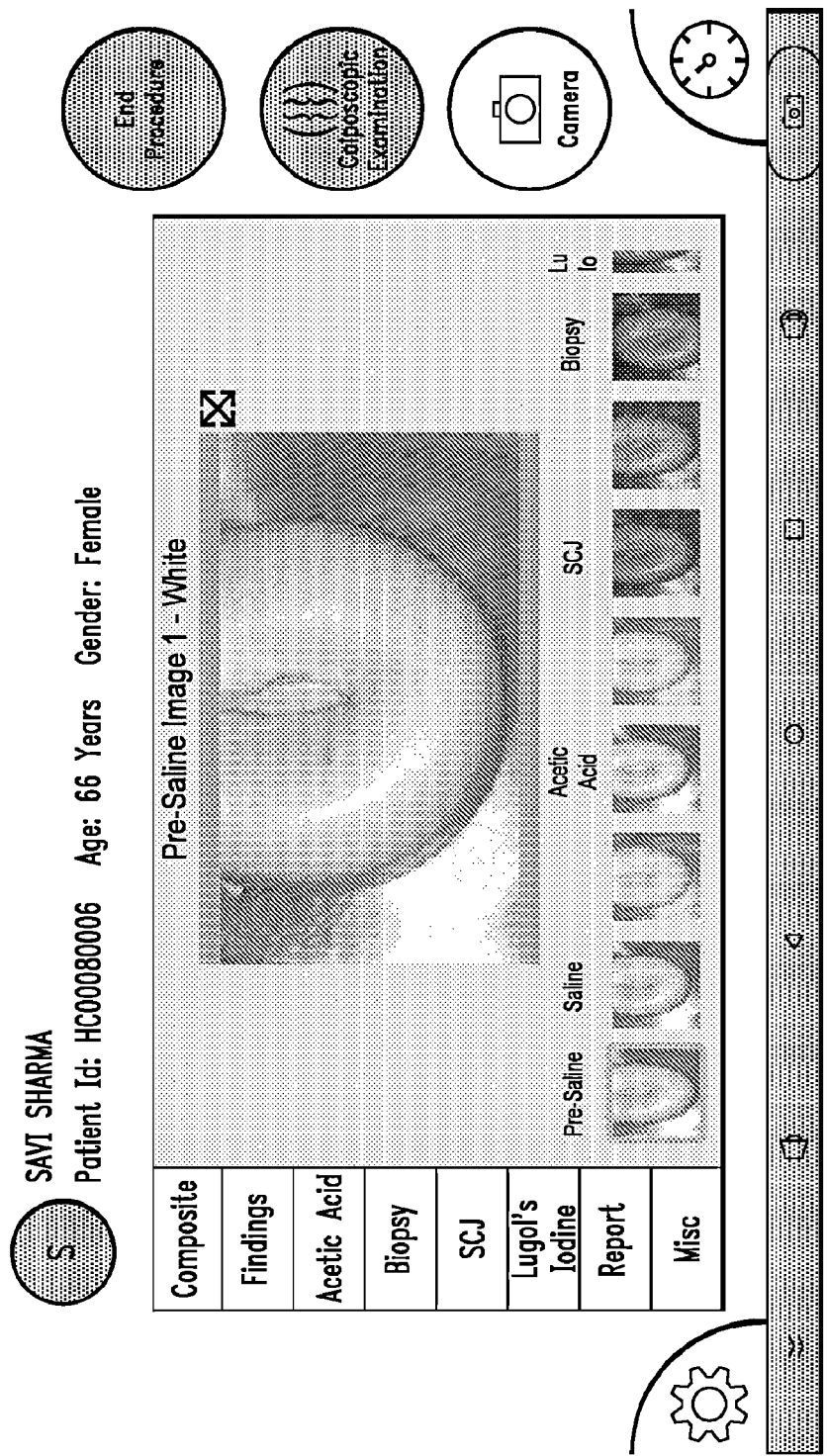
FIG. 17 illustrates an exemplary final report associated with the guided colposcopy procedure, the final report to be stored as part of the patient's electronic file and perhaps also printed out, as necessary.

Also shown in the screen shot of FIG. 15 is an "end procedure" prompt 82. Once activated by the medical personnel, a confirmation screen 84 may be displayed (as shown in FIG. 16). Presuming that the procedure is indeed completed, the guided process next displays a summary of the procedure results, such as in the dashboard form illustrated in FIG. 17. The dashboard displays all of the images captured during the guided colposcopy procedure. All of the relevant patient identifying information is also shown on this dashboard view.

For experienced medical personnel, the various digital images may be recalled and manipulated using the scroll bars and button features as shown. In some applications, specific software associated with image recognition may be utilized to indicate medically-relevant ROIs. These may include, for example, the extent of whiteness in the cervical images, particularly as a result of acetic acid uptake, as well as the location of the cervical OS.

For less-experienced medical personnel, these tools are useful to aid in detecting diagnostically-relevant features in an image, where these individuals are guided by an information pop-up that displays succinct instructions on how to use these tools. It is an aspect of the present invention that any clinician having authenticated access to the stored information (which may be on a secure network server) may review the data. Thus, the procedure may take place on one continent, and the review of the captured images performed on another continent. There is also the capability of adding notes to the file history, and directly write on the digital images (for example, to encircle medically relevant features).

Figure 18:
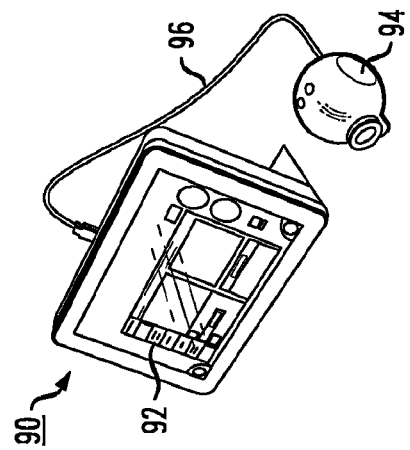
FIG. 18 illustrates an exemplary colposcopy instrument that may be used to perform the guided colposcopy procedure in accordance with the present invention, including a tablet device (with the guided procedure installed in the device) and an associated digital camera peripheral device under the control of the table device.

FIG. 18 illustrates an exemplary tablet device 90 that may be configured in accordance with the principles of the present invention to include the software program required to perform the guided colposcopy procedure. In the particular view of FIG. 18, tablet device 90 is shown as including a touchscreen 92, used to display the various screen shots as described above as the guided colposcopy procedure progresses along the defined milestones of progression timeline 40. An exemplary digital camera peripheral device 94 is shown as coupled to tablet device 90 via a communication link 96 (such as a cabled USB connection). In accordance with the principles of the present invention, digital camera 94 is controlled by tablet device 90 to capture the various digital images (still and video) in the manner described above.

Figure 19:
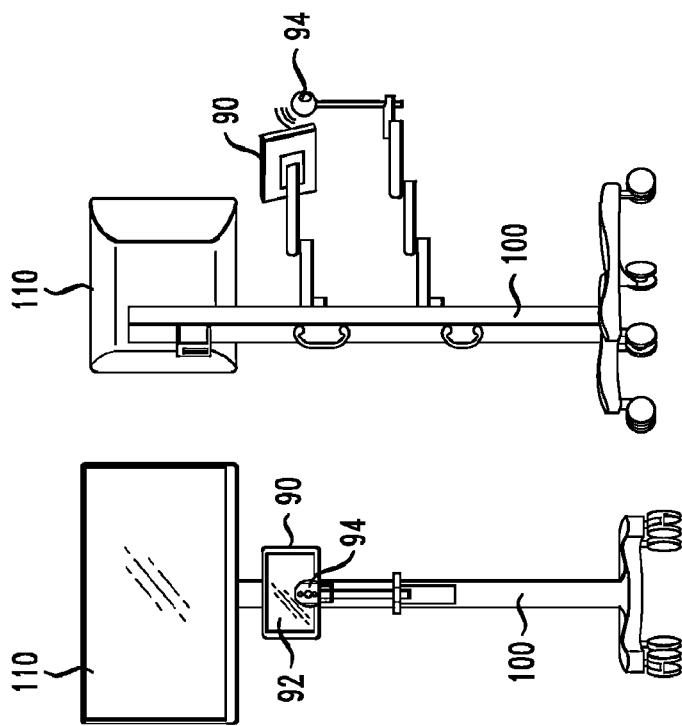
FIG. 19 contains front and rear illustrations of the instrument of FIG. 16 as mounted on a portable rack that may be moved from one exam room to another, as necessary.

FIG. 19 illustrates an exemplary arrangement of the components of the guided colposcopy instrument as may be found in a medical office or clinic environment. In particular, FIG. 19 illustrates tablet 90 and digital camera peripheral device 94 as mounted on a portable instrument rack 100, both a front view and an isometric rear view included in the view of FIG. 19. In this particular arrangement, an additional flat screen display 110 is included as part of the instrumentation, allowing for additional medical personnel to easily view the guided colposcopy procedure in real time. Moreover, as mentioned above, tablet device 90 may be in communication with remotely-located computing devices (authenticated devices), allowing for additional real-time consultation, as well as off-site storage and retrieval of the final report of the guided colposcopy procedure.

In the configuration of FIG. 19, a low-energy wireless (e.g., WiFi) connection is used between tablet device 90 and digital camera 94 to control the movement and adjustments of the camera during the procedure to create the required digital images (still images and video) at the appropriate points in time. Again, the ability to provide a standardized method of obtaining and recording the digital images (including the specific lighting and camera settings, provided as metadata associated with the image capture) allows for the system of the present invention to create consistent and standardized data collection for use in performing a diagnosis.

Summarizing, by recognizing the importance of standardization for consistent image analysis and diagnosis, integrated software within the colposcopy instrument as formed in accordance with the present invention thus prompts the medical personnel to capture relevant images in guided (prompted) sequential process that includes timing of the acetic acid uptake. The entire guided colposcopy procedure may take less than two minutes. This ensures that appropriate, relevant, and high-quality images of the cervix are taken for more accurate analysis by inbuilt computational software and doctors.

As mentioned above, a range of circumstances and training exist for health care workers in different settings, and the software-guided colposcopy apparatus of the present invention is designed to support the less experienced medical personnel during colposcopy. The guided flow can also be easily used by an experienced doctor to train someone that is less experienced. As shown in FIGS. 1-17, the tablet/computing device utilizes a unique, easy-to-use user interface that guides the medical personnel through a series of clear screen prompts to capture key images during the exam.

The procedure, once begun, is automated and does not require the individual to make decisions about when to capture an image. The relevant images are displayed to the medical personnel at the end of the procedure. This includes images taken before, during, and after acetic acid application, a video (if recorded) of the acetic acid uptake by the tissue, images of the SCJ, and an image after application of Lugol's iodine.

Standardization, consistency, and collection of all relevant images can reduce the subjectivity and variability in diagnostic assessment that otherwise abounds without a guided flow and series of image capture prompts; this is particularly vital for colposcopy and cervical precancer screening where a set of images are expected to be taken for quality assurance.

While various embodiments of the present invention have been described above, it should be understood that they have been presented by way of example only, and not limitation. Thus, the breadth and scope of the present invention is not considered to be limited by any of the above-described embodiments, but should be defined only in accordance with the claims appended hereto.

What is claimed is:

1. A method for carrying out a guided colposcopy procedure utilizing a combination of a digital camera and computer-controlled colposcopy instrument including a display screen, the method comprising:
    initiating the computer-controlled colposcopy instrument to display a plurality of selectable options associated with a set of defined steps in the guided colposcopy procedure including at least the sequential steps of: (1) saline swabbing of the cervix of a patient, and (2) performing an acetic acid uptake;
    selecting values for each option of the plurality of selectable options presented on the display;
    commanding the computer-controlled colposcopy instrument to activate the digital camera so as to present a digital image of a cervix region of interest (ROI) on the display;
    presenting a set of timeline milestones as an overlay on the digital image, each milestone associated with an individual step of the set of defined steps in the guided colposcopy procedure;
    prompting medical personnel performing the guided colposcopy procedure through each individual step, changing the visual display of each milestone as its associated step is completed;
    collecting digital images of the cervix ROI during the set of defined steps in the guided colposcopy procedure, as prompted by the computer-controlled colposcopy instrument, forming a plurality of digital images including sets of digital images associated with various steps; and
    creating a final report of the colposcopy procedure in tangible form, the final report including at least a listing of selected options and selected ones of the plurality of digital images of the cervix ROI captured during the procedure.

2. The method as defined in claim 1 wherein the plurality of selectable options includes a selection from among a listing of pre-defined time intervals for capturing images during the acetic acid uptake step.

3. The method as defined in claim 2 wherein the plurality of selectable options further includes an acetic acid concentration selection for use in the acetic acid uptake step from among a listing of pre-defined acetic acid.

4. The method as defined in claim 3 wherein the acetic acid concentration selection includes a fill-in option for manual entry by medical personnel.

5. The method as defined in claim 2, wherein the step of collecting digital images includes automatic capturing of digital images of acetic acid uptake during the selected, pre-defined time interval, allowing for an assessment of the impact rate of acetic acid uptake on the eventual diagnostic recommendation.

6. The method as defined in claim 2 wherein the plurality of selectable options further includes a selection of whether or not to include a Lugol's iodine step.

7. The method as defined in claim 2 wherein the plurality of selectable options further includes a selection of allowing or disallowing audio prompts during the guided colposcopy procedure.

8. The method as defined in claim 7 wherein the audio prompting further includes the capability of performing speech recognition from the medical personnel.

9. The method as defined in claim 8 wherein speech recognition is utilized to record procedure notes dictated by the medical personnel for inclusion in the created final report.

10. The method as defined in claim 2 wherein the plurality of selectable options further includes a selection of whether or not to overlay a reference box over the cervix ROI as presented on the display screen.

11. The method as defined in claim 10, wherein upon selection to include the reference box, the method comprises the further step of:
    commanding the computer-controlled colposcopy instrument to display a set of camera settings for use by the medical personnel to adjust focusing and lighting of the cervix in the digital image, and centering of the cervix within the reference box on the display.

12. The method as defined in claim 10, wherein upon selection to include the reference box, the method comprises the further step of:
    utilizing digital image processing capabilities of the computer-controlled colposcopy instrument to automatically detect the cervix and adjust the camera settings to position the cervix within the reference box for improved focusing and lighting.

13. The method as defined in claim 1 wherein the method further comprises
    presenting camera controls on the display screen; and
    adjusting the focus/lighting of the displayed cervix ROI in response to the medical personnel's use of the presented camera controls.

14. The method as defined in claim 1 wherein the method further comprises
    presenting camera controls on the display screen; and
    utilizing digital image processing capabilities of the computer-controlled colposcopy instrument to automatically adjust the focus/lighting of the displayed cervix ROI to optimize the presentation of the digital image.

15. The method as defined in claim 1 wherein the method further comprises
    presenting, on the display screen subsequent to the acetic acid uptake step, a selectable option to perform a biopsy prior to creating the final report.

16. The method as defined in claim 15 wherein the biopsy process includes the steps of
    commanding the computer-controlled colposcopy instrument to perform the following: (1) display a reference grid over the digital image of the cervix ROI and (2)

present a marking tool controllable by the medical personnel to indicate a location of a biopsy on the reference grid; and storing information associated with the location of the biopsy in the created final report.

17. The method as defined in claim 1 wherein the step of creating the final report includes activating selected captured images for further review and notation of relevant information for inclusion in the final report.

18. The method as defined in claim 1 wherein the method further comprises the step of:

storing the created final report in an electronic file associated with the patient.

19. The method as defined in claim 18 wherein the method further comprises the step of:

saving the electronic file in a system accessible by authenticated medical personnel.

20. The method as defined in claim 1 wherein the method further comprises the step of:

retrieving electronically-stored patient history information for review during the guided colposcopy process.

* * * * *